(12) United States Patent
Benford

(10) Patent No.: US 11,179,262 B2
(45) Date of Patent: Nov. 23, 2021

(54) ANKLE SUPPORT DEVICE

(71) Applicant: Jacob Benford, Aptos, CA (US)

(72) Inventor: Jacob Benford, Aptos, CA (US)

( * ) Notice: Subject to any disclaimer, the term of this patent is extended or adjusted under 35 U.S.C. 154(b) by 0 days.

(21) Appl. No.: 16/841,844

(22) Filed: Apr. 7, 2020

(65) Prior Publication Data

US 2020/0229959 A1 Jul. 23, 2020

Related U.S. Application Data

(62) Division of application No. 14/304,458, filed on Jun. 13, 2014, now Pat. No. 10,610,398.

(60) Provisional application No. 61/957,703, filed on Jul. 11, 2013.

(51) Int. Cl.
*A61F 5/01* (2006.01)

(52) U.S. Cl.
CPC .................. *A61F 5/0127* (2013.01)

(58) Field of Classification Search
CPC .... A61F 5/0111; A61F 5/0113; A61F 5/0127; A43B 7/20
USPC .......................................... 602/89, 107, 76 R
See application file for complete search history.

(56) References Cited

U.S. PATENT DOCUMENTS

| | | | | |
|---|---|---|---|---|
| 589,253 A * | 8/1897 | Engberg | | |
| 1,332,047 A * | 2/1920 | Lasher | ................. | A61F 5/0113 602/27 |
| 4,753,229 A * | 6/1988 | Sutherland | ............ | A61F 13/066 602/27 |
| 4,922,630 A * | 5/1990 | Robinson | ................. | A43B 5/00 36/89 |
| 4,936,295 A * | 6/1990 | Crane | ................... | A61F 5/0111 36/89 |
| 4,989,350 A * | 2/1991 | Bunch | ...................... | A43B 5/00 36/114 |
| 5,672,156 A * | 9/1997 | Jimenez Ramos | ...... | A43B 7/20 36/89 |
| D457,639 S * | 5/2002 | McCoy | ........................ | D24/192 |
| 8,904,674 B2 * | 12/2014 | Schwartz | .............. | A61F 5/0127 36/89 |
| 10,610,398 B2 * | 4/2020 | Benford | ................ | A61F 5/0127 |
| 10,945,871 B2 * | 3/2021 | Patterson | .............. | A61F 5/0127 |

* cited by examiner

*Primary Examiner* — Camtu T Nguyen
(74) *Attorney, Agent, or Firm* — Donald R. Boys; Central Coast Patent Agency LLC

(57) ABSTRACT

An ankle-bracing apparatus has a support plate curved to fit on the medial aspect of a user's lower leg, a shoe having a sole, a medial side, a lateral side and a vertical extension attached on the medial side, presenting a pivot point near an uppermost end, a strut extending downward from the medial side of the support plate with a fastener near a lowermost end joined pivotally to the pivot point on the vertical extension, a lateral strut extending vertically on the lateral side of the shoe, in line with the user's lateral malleola, a strap buckle secured at an upper end of the lateral strut, presenting a laterally extending opening, and a strap arrangement joining the strap buckle to a first and a second anchor point on the medial side of the curved support plate.

6 Claims, 5 Drawing Sheets

ANKLE SUPPORT DEVICE

CROSS-REFERENCE TO RELATED DOCUMENTS

This application is a divisional application of U.S. application Ser. No. 14/304,458, filed on Jun. 13, 2014, which claims priority to Provisional Patent Application 61/957,703, filed on Jul. 11, 2013. The entire disclosure of both parent applications is incorporated at least by reference.

BACKGROUND OF THE INVENTION

1. Field of the Invention

The present invention is in the field of sports medicine and pertains particularly to methods and apparatus for preventing occurrence or re-injury of a lateral ankle sprain.

2. Discussion of the State of the Art

Ankle sprains caused by sports injuries are one of the more common types of injuries seen. Ankle sprains generally require some type of artificial support to allow for immobilization of the ankle joint in the direction of the sprain and enough time for lateral ligaments of the ankle to heal. Continued inversion and supination of the sprained joint laterally can prevent healing and cause re-injury.

Aftermarket solutions for persons with an ankle sprain include soft and rigid braces as well as numerous varieties of tapes and ankle wrapping materials. Limitations exist with current ankle support devices for example: casts and braces may be too bulky such that the wearer must go without a shoe on the injured foot at least for a period of time. Many ankle braces may include various hardware components that may become damaged or lost during use. Many available braces cannot be used with sport shoes in active participation, and many braces do not offer sufficient support.

Therefore, what is clearly needed is an ankle support apparatus that is versatile and can provide lateral support without limiting function or plantar and dorsiflexion.

BRIEF SUMMARY OF THE INVENTION

In one embodiment an ankle-bracing apparatus is provided, comprising a support plate curved substantially 180 degrees to fit on the medial aspect of a user's lower leg above the ankle, open to the lateral aspect of the leg, a shoe shaped to enclose the user's foot, the shoe having a sole, a medial side, a lateral side and a vertical extension attached on the medial side, the vertical extension presenting a pivot point near an uppermost end, a strut extending downward from the medial side of the support plate, the strut having a fastener near a lowermost end joined pivotally to the pivot point on the vertical extension from the medial side of the shoe, a lateral strut extending vertically on the lateral side of the shoe, in line with the user's lateral malleola, fastened securely to the lateral side of the shoe, a strap buckle secured at an upper end of the lateral strut at a height of the user's plantar/dorsiflexion fulcrum, the strap buckle presenting a laterally extending opening of a length to accept a width of one or more straps, and a strap arrangement joining the strap buckle to a first and a second anchor point on the medial side of the curved support plate, the strap arrangement having a first strap portion adapted to pass in front of the leg and a second strap portion adapted to pass behind the leg.

In one embodiment one of the first and the second strap portions has an adjustment mechanism adapted to shorten and lengthen the strap portion, adjusting tension on the strap arrangement. Also, in one embodiment the lateral strut is built into the lateral side of the shoe. Also, in one embodiment the lateral strut is attached to the lateral side of the shoe by heat welding, or by adhesive. In one embodiment an inside surface of the support plate is lined with a padding material. And in one embodiment the shoe is a sports shoe.

DETAILED DESCRIPTION

In various embodiments described in enabling detail herein, the inventor provides an ankle bracing apparatus. The present invention is described using the following examples, which may describe more than one relevant embodiment falling within the scope of the invention.

Figure 1:
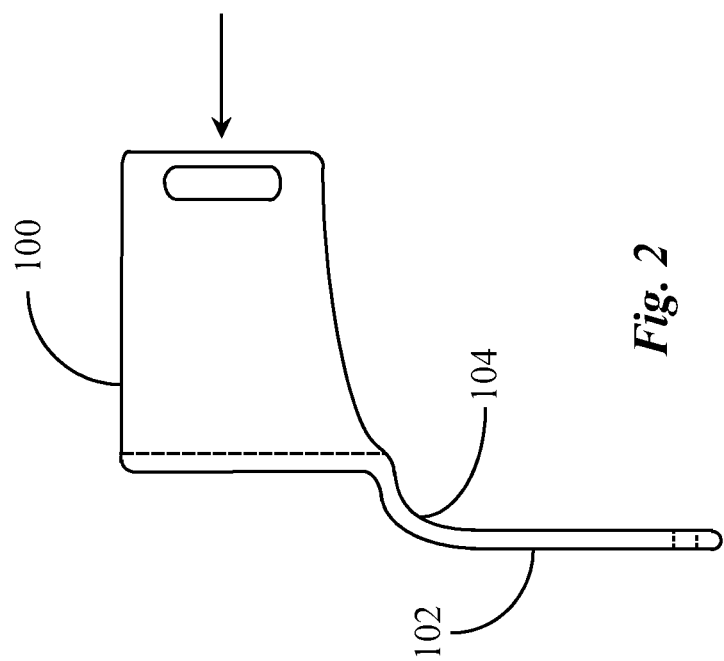
FIG. 1 is a perspective view of a support plate according to an embodiment of the present invention.

FIG. 1 is a perspective view of a curved support plate, which is a part of an ankle bracing assembly according to an embodiment of the present invention. Support plate 100 may be stamped from sheet metal, formed from a relatively rigid polymer material, or may be made from plastic or carbon fiber reinforced material. In one embodiment semi-rigid materials like rubber may be used. Support plate 100 is shaped to provide a collar or U-shaped feature formed or shaped in the material for the function of locating against a lower leg of the wearer above the wearer's ankle in a correct orientation for use. Support plate 100 in one embodiment includes a strut 102 contiguously formed thereon or rigidly affixed thereto by nut and bolt or other fastening mechanisms or processes.

Support plate 100 in one embodiment includes two anchor slots 101 for connecting a leg strap (not illustrated here for clarity). The leg strap, described in more detail below, may be attached to the support plate in a variety of different ways. The U-shaped feature encompasses the user's lower leg not far above the ankle. In proper orientation on the user's leg, the back wall or surface of the collar faces inward against the user's medial part of the lower leg. In this configuration strut 102 extends downward and over the medial side of a shoe or other integrated footwear. Strut 102 includes at least one through opening 103. Through opening 103 may be attached to a Medial strut (not illustrated) when installing the support plate to an article of footwear, which is described in more detail below, or may be attached to a medial strut from a footplate.

Figure 2:
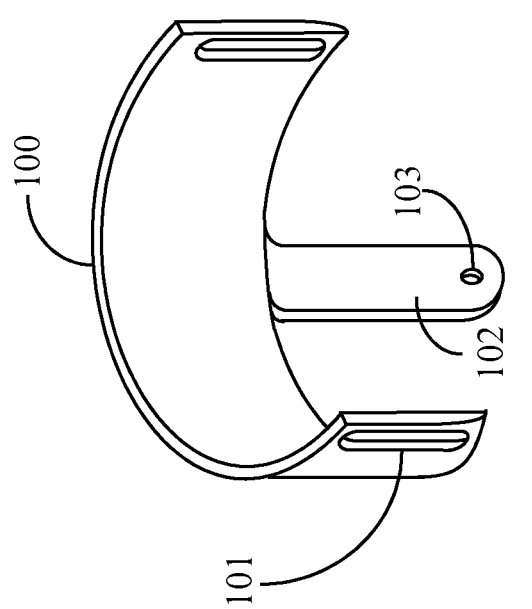
FIG. 2 is a side elevation view of the support plate of FIG. 1.

FIG. 2 is a side elevation view of the support plate of FIG. 1. Support plate 100 is illustrated in side view with an arrow pointing into the open side of the collar. In this embodiment strut 102 has a shoulder 104 of a radius that is sufficient to clear the edge of the footwear the device with which the ankle bracing apparatus may be integrated. The bottom portion of the strut fits roughly over the inside (arch side) of the user's footwear in this example (footwear not illustrated here for clarity). Shoulder 104 may be molded into the support plate or formed therein by material bending processes.

The actual shape of the leg-collar feature may vary widely without departing from the spirit and scope of the invention. In one embodiment a semi-annular collar has multiple flat sections aggregating to form the collar. In another embodiment a three-sided or U-shaped profile may be used. In still another embodiment a half circle is used. Support plate 100 prevents the ankle from re-injury by providing an anchor for straps to support against inverting or supinating the ankle in the direction of the outside lateral edge of the foot, as is described in more detail below.

Figure 3:
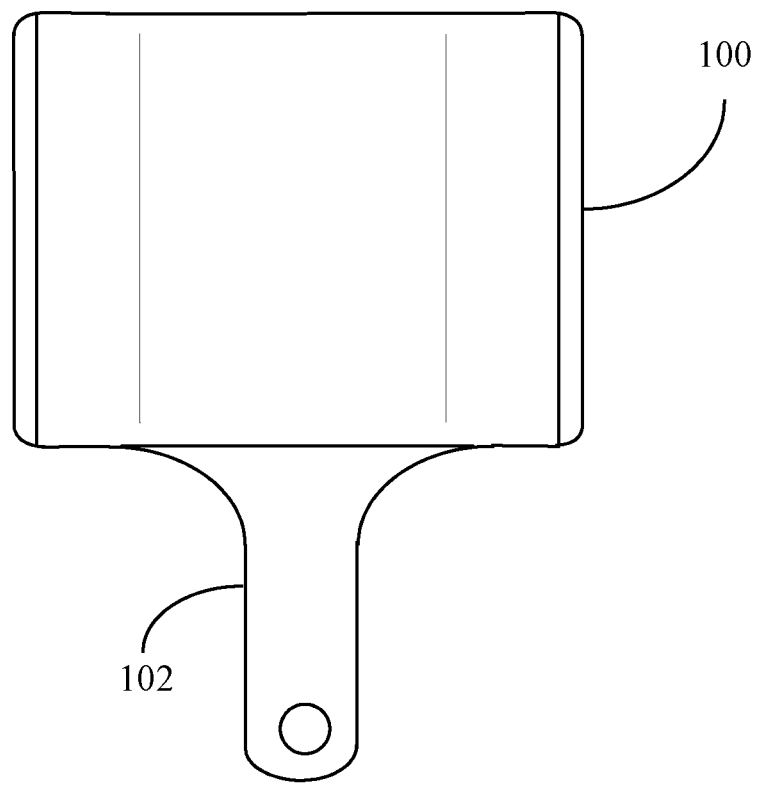
FIG. 3 is a front elevation view of the support plate of FIG. 1.

FIG. 3 is a front elevation view of the support plate of FIG. 1. Support plate 100 may be coated on the inside surfaces that interface with the user's leg. The coating may be a moisture-absorbing soft material or rubber foam or like materials to provide comfort when wearing the device and when walking with the device. Such a coating might be sprayed or glued onto the inside surface of the leg collaring feature. The rest of the inside surface of the support plate may be left bare or equally coated. In one embodiment the user may wear a flexible material collar over the leg and then insert the support plate onto the leg over the material collar.

Figure 4:
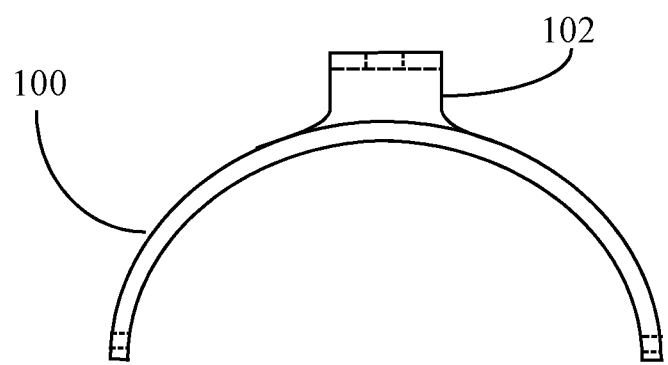
FIG. 4 is an overhead view of the support plate of FIG. 1.

FIG. 4 is an overhead view of the ankle support plate of FIG. 1. In this overhead view the offset amount of strut 102 from the back surface of ankle support plate 100 is visible. The offset amount simply provides room for the user to wear a shoe like a running shoe and have strut 102 secured to the medial aspect of the shoe. In one embodiment support plate 100 is semi-rigid and malleable to be manually shaped to fit the inside of a wearer's leg. In one embodiment the support plate is somewhat resilient and can be flexed out ward to fit over and grip the inside of the wearer's leg. In still another embodiment the leg-collar portion of the ankle support plate is adjustable to increase or decrease the radius of the collar.

Figure 5:
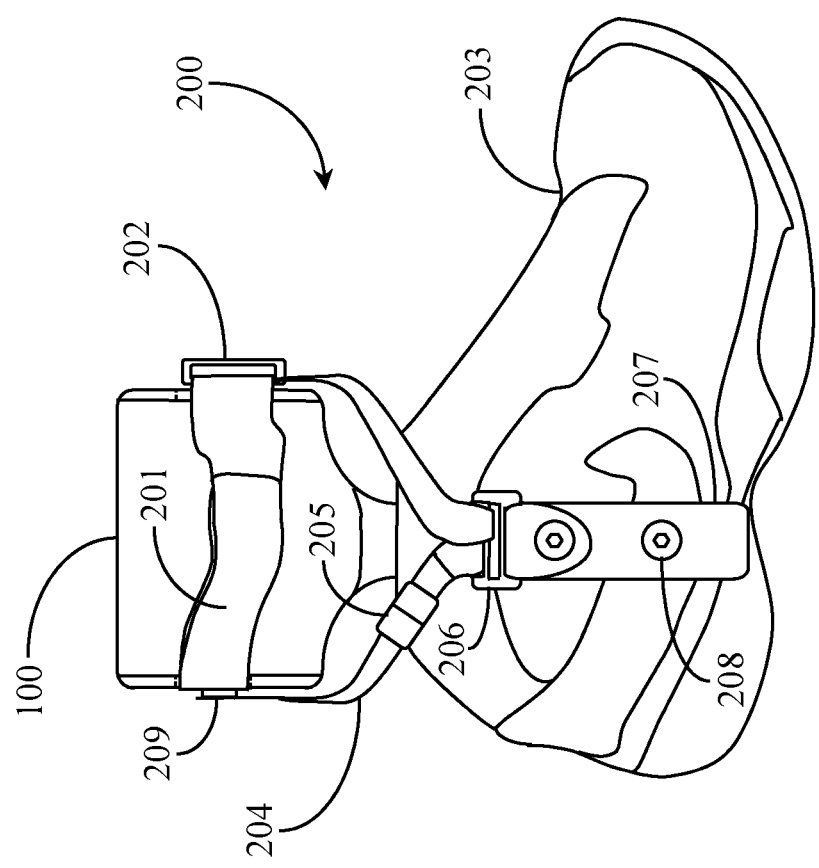
FIG. 5 is a lateral elevation view of an ankle bracing apparatus including the support plate of FIG. 1 secured to a sports shoe 203.

FIG. 5 is a lateral elevation view of an ankle bracing apparatus 200 including the ankle support plate 100 of FIG. 1 secured to a sports shoe 203, and including other elements. Support plate 100 may be secured to an article of footwear, in this example, shoe 203. Shoe 203 has a lateral strut 207 secured to the outside lateral surface of the shoe in line with the lateral malleola. Lateral strut 207 may be stamped or formed from sheet metal in one embodiment. In another embodiment, lateral strut 207 is molded using a rigid polymer, or may be fashioned from a plastic or a carbon-fiber material.

Lateral strut 207 includes at least one through opening for accepting a fastener 208 to secure lateral strut 207 to shoe 203. The lateral strut in different embodiments may be built into the shoe, or connected in some fashion proximally to prevent migration. Lateral strut 207 may also be manufactured from a heat weld material that may be heat welded to the rubberized heel of running shoe 203. Lateral strut 207 may also be glued to the outside surface of running shoe 203 without departing from the spirit and scope of the present invention. Lateral strut 207 retains or is connected to a strap buckle 206.

In one embodiment, a portion of lateral strut 207 may be threaded through one side of the strap buckle and may be folded or urged over onto itself and fastened using a fastener 208 retaining the strap buckle for use in tensioning the ankle support device. The hinge for the lateral strut and strap loop is approximately at plantar/dorsiflexion fulcrum of the ankle. In this embodiment the rotatably attached fastener is the lower fastener connecting the lateral strut to shoe 203. The rotatable attachment enables plantar and dorsi flexing of the ankle while walking or running. In another embodiment the upper fastener may be rotatably attached to a strap buckle such as strap buckle 206 allowing for plantar and dorsiflexion of the ankle.

Fastener 208 may be a rivet, a screw, a snap or another type of fastening mechanism without departing from the spirit and scope of the present invention. Fastener 208 may serve as a freely rotatable fastener allowing for plantar and dorsiflexion of the ankle while walking or running as described above. It is noted herein that there are two fasteners 208 on lateral strut 207 in this example, the lower one for fastening the lateral strut to shoe 203 and the upper one for fastening the strut to the strap buckle. It is noted herein that fasteners share the same element number and may be the same type of fasteners.

Support plate 100 is secured to the medial surface of the shoe via a medial strut to which strut 102 of support plate 100 (not visible in this view) is fastened. Support plate 100 is depicted in correct orientation for integration with running shoe 203. That is to say the open collar portion of the support plate interfaces with the medial side of the wearer's leg (wearer's leg not illustrated in this example for clarity). A tensioning strap 204 is anchored on opposite sides of the collar of support plate 100 and threaded through strap buckle 206. Tensioning strap 204 may be connected and adjusted for length using a strap connector and length adjustment mechanism 205. Tension on strap 204 can be adjusted that will change the distance between plate 100 and lateral strut 207.

Strap 204 may be fabricated or cut from a heavy fabric. In one embodiment strap 204 is fabricated from a polymer material that is not elastic. Strap 204 is anchored at both ends of the collar portion of support plate 100 using strap anchors 209 (one on each side). Strap 204 is threaded through strap buckle 206. Support plate 100 is also depicted with a leg strap 201. Strap 201 may be extended to wrap about the leg of the wearer and be adjusted for fit using a length adjustment mechanism 205. Strap 201 secures the support plate to the wearer's leg. Mechanism 205 may also serve to connect strap 204 together from two separate lengths of strap.

Strut 102 of ankle support plate 100 is connected on the medial side of shoe 203 using a medial strut 301 (see FIG. 6) mounted to the running shoe. Therefore, with the medial aspect of shoe 203 secured to the support plate, the wearer may connect straps 204 to strap buckle 206 and adjust the strap lengths using mechanism 205, which may also be used to tighten strap 204 increasing tension in the direction opposite the medial side of running shoe 203 to prevent rolling of the ankle. Fastener 208 and a similar fastener for the strut on the other side of shoe 203 may be rotatably attached to the connector plate to allow plantar and dorsiflexion flexing of the ankle while walking.

Figure 6:
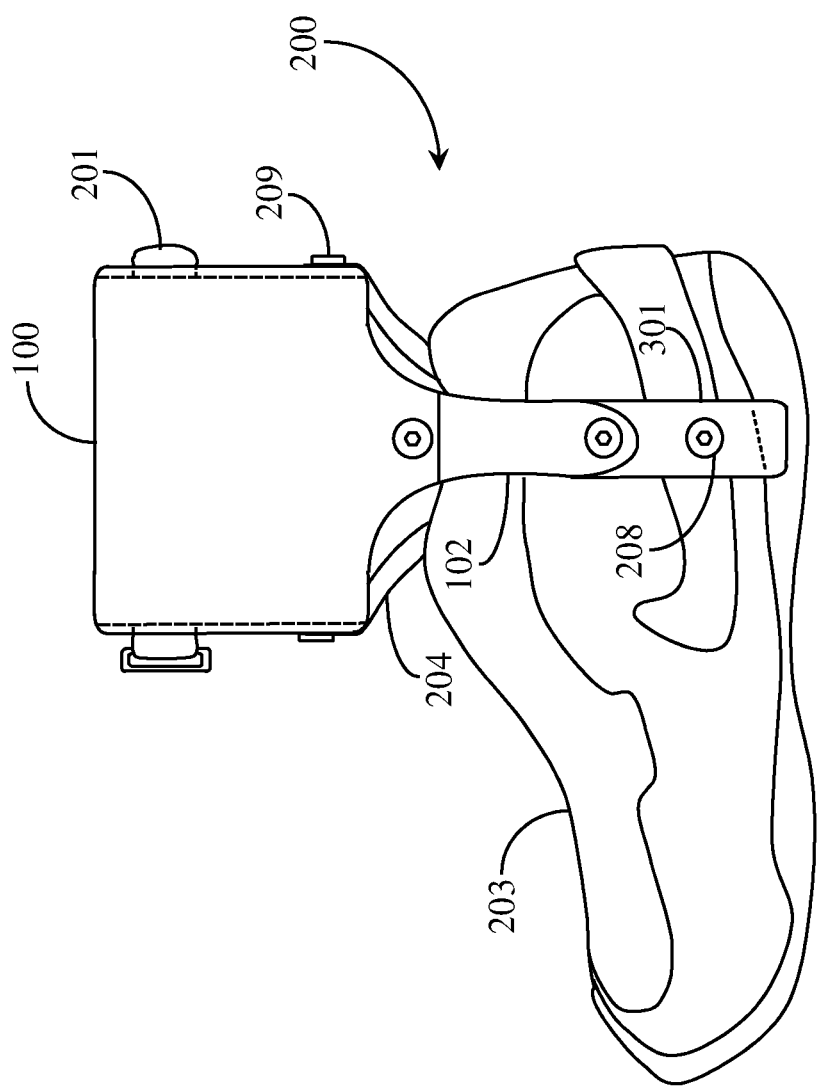
FIG. 6 is a medial elevation view of the ankle bracing apparatus of FIG. 5 including the support plate of FIG. 1 secured to sports shoe 203.

FIG. 6 is a medial elevation view of support apparatus 200 of FIG. 5 including support plate 100 of FIG. 1 secured to shoe 203. Strut 102 of support plate 100 is fastened to a medial strut 301 using a fastener 208. Fastener 208 may be a screw, rivet, or retaining pin. Strut 102 may be rotatably attached to connector plate 301 to enable plantar and dorsiflexion ankle flex while walking.

Medial strut 301 may be stamped or formed from sheet metal in one embodiment. In another embodiment, medial strut 301 is molded using a rigid polymer or plastic or carbon fiber. Medial strut 301 includes at least one through opening for accepting a fastener 208 to secure medial strut 301 to shoe 203. Medial strut 301 may also be manufactured from a heat weld material that may be heat welded to the rubberized heel of shoe 203. Medial strut 301 may also be glued to the outside surface of running shoe 203 without departing from the spirit and scope of the present invention. In this view, ankle support plate 100 is facing away from the viewer with respect to the open collar portion of the plate. The support plate seats against the inside of or the medial side of the wearer's leg. Medial strut 301 in one embodiment is fashioned to bear at the lower end on the sole of shoe 203.

Figure 8:
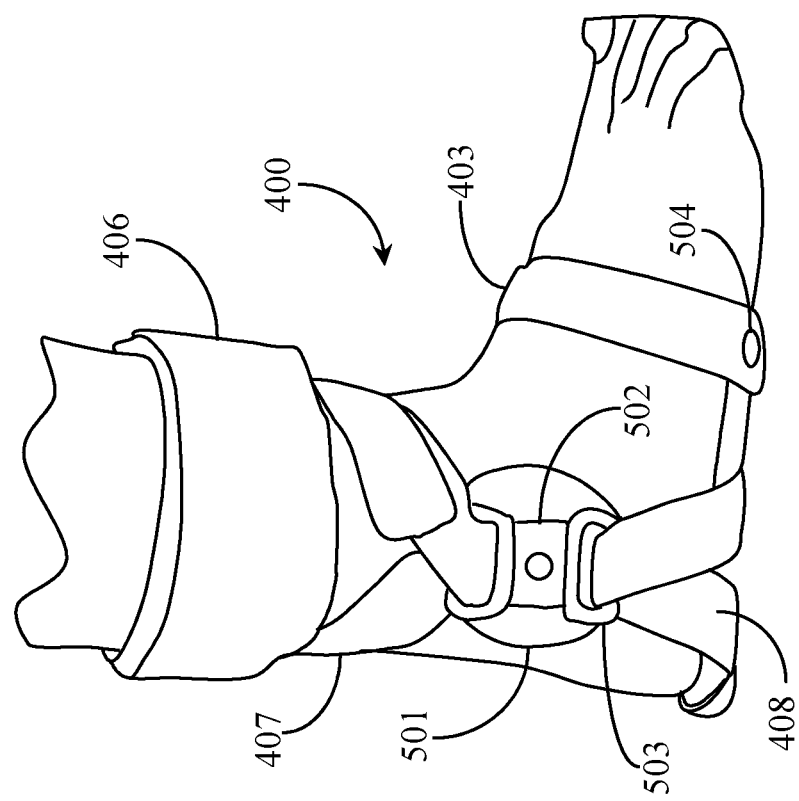
FIG. 8 is a lateral elevation view of the ankle bracing apparatus of FIG. 7 secured to the footplate of FIG. 7.
Figure 7:
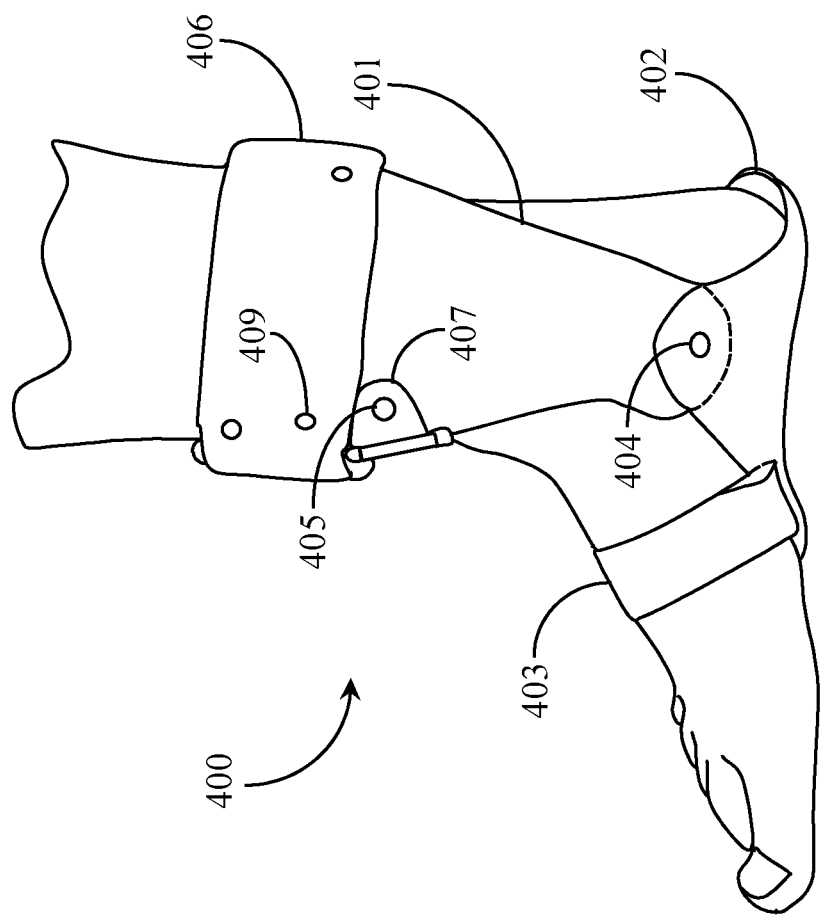
FIG. 7 is a medial elevation view of an ankle bracing apparatus secured to a footplate according to an embodiment of the present invention.

FIG. 7 is a medial elevation view of an ankle support apparatus 400 secured to a footplate according to an embodiment of the present invention, viewed in one direction. FIG. 8 is a lateral elevation view of ankle support apparatus 400 of FIG. 7 viewed in the opposite direction. Referring now to FIG. 7, apparatus 400 functions by the same principle as the apparatus described in FIGS. 1 through 6. Apparatus 400 includes an ankle support plate 401 similar to plate 100 accept that it is a straighter strut with little or no shoulder for offsetting the strut of the plate to fit the outside of a running shoe. In this embodiment apparatus 400 may be used while not wearing a shoe or the wearer may put on a shoe over the apparatus.

Ankle support plate 401 includes a leg-collar portion and strut portion with a through opening for accepting a fastener 404. Ankle support plate 401 may be formed from or stamped from sheet metal or made from a substantially rigid polymer material, plastic or carbon fiber. In one embodiment semi-rigid materials like rubber may be used. Ankle support plate 401 is shaped to provide a collar or U-shaped feature formed or shaped in the material for the function of locating against the leg of the wearer in a correct orientation for use.

Support plate 401 includes two anchor slots (not visible) for connecting a leg strap 406, just as described above for the embodiments of FIGS. 1-6. The U-shaped feature encompasses the user's lower leg not far above the ankle. In proper orientation on a user's leg, the back wall or surface of the collar faces inward against the user's medial part of the lower leg. In this configuration, the strut portion extends downward to and is rotatably connected to a footplate 402 using a fastener 404. In this embodiment, footplate 402 is provided to complete the tensioning circuit, and takes the place of the shoe in the embodiments described above with reference to FIGS. 1-6. Footplate 402 may be fabricated from sheet metal, rubber polymer or any other material that is rigid or semi-rigid.

Footplate 402 has a medial strut extending upward from the arch of the wearer's foot to provide a connecting location in place of the medial strut off the shoe base as was described previously, hinged approximately at the medial plantar/dorsiflexion fulcrum of the ankle. Referring to FIG. 8, footplate 402 includes a strap anchor 504 for anchoring a foot strap 403 to the lateral side of the footplate. Referring back to FIG. 7, footplate 401 includes a strap slot on the medial side to enable strapping the front part of the wearer's foot down to the footplate. Footplate 402 may be shaped to generally conform to the shape of the wearer's foot and may be inserted into the bottom heel portion of a shoe similar to running shoe 203 or any other similar footwear appropriate for normal walking posture. In this respect, footplate 402 may have a relatively thin wall thickness.

Support plate 401 includes strap anchor 405 on opposite sides for securing tensioning straps to the support plate. Referring now to FIG. 8, tensioning straps 407 are connected to a strap buckle 503 on a strap retaining mechanism 502. Strap retaining mechanism 502 includes two buckles 503. Strap retaining mechanism 502 is mounted to a lateral malleola cup 501 to protect the user's ankle from the discomfort of interface with the buckle hardware. Lateral malleola cup 501 may be manufactured of a semi-rigid or rigid polymer, rubber, or other resilient materials. Lateral malleola cup 501 with strap retaining mechanism 502 has a thin profile to allow for insertion into footwear such as a running shoe without adding discomfort to the wearer.

Apparatus 400 also includes a connector strap 408 anchored at both ends to the underside of footplate 402 (anchor point not visible). Connector strap is threaded through a lower buckle on strap retaining mechanism 502. Referring now back to FIG. 7, ankle support plate 401 may include strap slots on opposing sides or the collar portion of the support plate for facilitating a leg strap 406 (slots covered by wrap). Leg strap 406 may be cut from a high grade strong but durable fabric. Fasteners 409 may be used to anchor leg strap 406 to the rear wall of ankle support plate 401.

Referring back to FIG. 7, fastener connection 404 provides a rotatable connection between footplate 402 and ankle support plate 401. The rotatable connecting point (404) enables plantar and dorsiflexion flex of the foot while walking. Referring now to FIG. 8, a user may apply tension to apparatus 400 by adjusting length of on straps 407, thus tightening or tensioning the apparatus to provide rigid ankle supports for the wearer. Once assembled on a user's foot, the user may put on a sock and a shoe. Referring now back to FIG. 7, it is noted that the inside of the leg-collar portion of ankle plate 401 may be lined or coated with a material designed to provide comfort and absorb moisture.

It will be apparent to one with skill in the art that the ankle support system of the invention in various embodiments may be provided using some or all of the mentioned features and components without departing from the spirit and scope of the invention. It will also be apparent to the skilled artisan that the embodiments described above are specific examples of a single broader invention that may have greater scope than any of the singular descriptions taught. There may be many alterations made in the descriptions without departing from the spirit and scope of the present invention.

It will also be apparent to the skilled person that the arrangement of elements and functionality for the invention is described in different embodiments in which each is exemplary of an implementation of the invention. These exemplary descriptions do not preclude other implementations and use cases not described in detail. The elements and functions may vary, as there are a variety of ways the hardware may be implemented and in which the software may be provided within the scope of the invention. The invention is limited only by the breadth of the claims below.

What is claimed is:
1. An ankle-bracing apparatus, comprising:
a support plate curved substantially 180 degrees adapted to fit on the medial aspect of a user's lower leg above the ankle, open to the lateral aspect of the leg;
a shoe adapted to enclose the user's foot, the shoe having a sole, a medial side, a lateral side and a vertical extension attached on the medial side, the vertical extension presenting a pivot point near an uppermost end;

a strut extending downward from the medial side of the support plate, the strut having a fastener near a lowermost end joined pivotally to the pivot point on the vertical extension from the medial side of the shoe;

a lateral strut extending vertically on the lateral side of the shoe, adapted to be in line with the user's lateral malleola, fastened securely to the lateral side of the shoe;

a strap buckle secured at an upper end of the lateral strut at a height of the user's plantar/dorsiflexion fulcrum, the strap buckle presenting a laterally extending opening of a length to accept a width of straps joining the strap buckle to a first and a second anchor point on the medial side of the curved support plate, the straps comprising a first strap adapted to pass in front of the leg and a second strap adapted to pass behind the leg.

2. The ankle-bracing apparatus of claim 1 wherein one of the first and the second straps has an adjustment mechanism adapted to shorten and lengthen the strap, adjusting tension on the strap.

3. The ankle-bracing apparatus of claim 1 wherein the lateral strut is built into the lateral side of the shoe.

4. The ankle-bracing apparatus of claim 1 wherein the lateral strut is attached to the lateral side of the shoe by heat welding, or by adhesive.

5. The ankle-bracing apparatus of claim 1 wherein an inside surface of the support plate is lined with a padding material.

6. The ankle-bracing apparatus of claim 1 wherein the shoe is a sports shoe.

* * * * *